United States Patent [19]

Mason et al.

[11] Patent Number: 5,327,900
[45] Date of Patent: Jul. 12, 1994

[54] APPARATUS AND METHOD FOR DISCRIMINATING BETWEEN HEART RHYTHMS WITH SIMILAR ATRIAL AND VENTRICULAR RATES

[75] Inventors: David Mason, Lane Cove; David Bassin, Coogee, Australia; Anthony Murphy, Leechhardt, Australia; Anthony C. Stephens, Willoughby, all of Australia

[73] Assignee: Telectronics Pacing Systems, Inc., Englewood, Colo.

[21] Appl. No.: 875,161

[22] Filed: Apr. 28, 1992

[30] Foreign Application Priority Data

Nov. 1, 1991 [AU] Australia ................. 9243

[51] Int. Cl.$^5$ ......................... A61B 5/0464
[52] U.S. Cl. .............................. 128/705
[58] Field of Search ............ 128/697, 705, 419 PG, 128/419 D; 607/4, 5, 9

[56] References Cited

U.S. PATENT DOCUMENTS

| 4,665,485 | 5/1987 | Lundy et al. | 128/697 |
| 4,799,493 | 1/1989 | DuFault | 128/705 |
| 4,860,749 | 8/1989 | Lehmann | 128/419 PG |
| 4,875,483 | 10/1989 | Vollmann et al. | 128/419 PG |
| 4,960,123 | 10/1990 | Maker | 128/705 |
| 5,000,189 | 3/1991 | Throne et al. | 128/705 |
| 5,074,308 | 12/1991 | Sholder | 128/697 |
| 5,086,772 | 2/1992 | Larnard et al. | 128/419 D |
| 5,107,850 | 4/1992 | Olive | 128/705 |
| 5,193,550 | 3/1993 | Duffin | 128/705 |

FOREIGN PATENT DOCUMENTS

| 0469817 | 2/1992 | European Pat. Off. | A61N 1/362 |
| 9209331 | 6/1992 | PCT Int'l Appl. | A61N 1/368 |

Primary Examiner—William E. Kamm
Attorney, Agent, or Firm—Gottlieb, Rackman & Reisman

[57] ABSTRACT

An apparatus and a method for discriminating between tachycardias of physiological origin, and those of pathological origin having similar atrial and ventricular rates, are disclosed. The apparatus includes two sensing electrodes for registering the electrograms from the atrium and the ventricle of the heart. There is further included a signal processing element for determining the times of atrial and ventricular events, and an algorithm for classifying the heart rhythm. The algorithm includes a means for discriminating between different types of heart rhythms having overlapping ventricular rates and having similar atrial and ventricular rates. The method utilizes an analysis of the relationships between successive atrial and ventricular intervals (i.e., atrial-atrial (AA), ventricular-ventricular (VV) and atrial-ventricular (AV) intervals) in discriminating between such heart rhythms.

18 Claims, 5 Drawing Sheets

APPARATUS AND METHOD FOR DISCRIMINATING BETWEEN HEART RHYTHMS WITH SIMILAR ATRIAL AND VENTRICULAR RATES

FIELD OF THE INVENTION

This invention relates to implantable medical devices such as cardioverter/defibrillator/pacemakers which monitor cardiac rhythm using atrial and ventricular sensors. Such devices are able to supply therapy to a patient in the form of defibrillation, cardioversion, bradycardia pacing or antitachycardia pacing, either individually or in combination. In particular, the invention relates to an apparatus and method that utilize a classification technique which discriminates among rhythms having overlapping ventricular rates and having similar atrial and ventricular rates. Such rhythms may be either physiological (e.g., normal sinus rhythm (NSR)) or pathological (e.g., slow ventricular tachycardia (SLVT)), and therefore require discrimination. The device and method described herein perform this discriminatory function where the SLVT is either slow dissociated ventricular tachycardia (SDVT) or ventricular tachycardia (VT) with 1:1 retrograde conduction (VT1:1R).

BACKGROUND OF THE INVENTION

Some current medical devices designed to provide antitachycardia therapy have attempted to discriminate between physiological (e.g. NSR) and pathological cardiac rhythms (e.g., SLVT) using the heart rate sensed by a single ventricular sensor. U.S. Pat. No. 4,875,483 to W. Vollmann et al., entitled "Implantable Cardiac Pacer With Programmable Antitachycardia Mechanisms", which issued on Oct. 24, 1989, discloses such a device. However, techniques which are based solely on ventricular rate parameters are unable to distinguish between physiological and pathological rhythms that have overlapping ventricular rates. An important instance of this is normal sinus rhythm (a physiological rhythm) and slow ventricular tachycardia (a pathological rhythm). The addition of an atrial sensor providing atrial event information may overcome this particular problem, as is proposed in U.S. Pat. No. 4,860,749 to M. H. Lehmann, entitled "Tachycardia Detection for Automatic Implantable Cardioverter/Defibrillator With Atrial and Ventricular Sensing Capability", which issued on Aug. 29, 1989. The device disclosed in U.S. Pat. No. 4,860,749 offers only a partial solution to this problem by classifying the rhythm as VT1:1R when the AV interval exceeds the sinus AV interval, provided the ventricular cycle length exceeds a crossover value. The device described in U.S. Pat. No. 4,860,749 is, however, still not capable of identifying SDVT and, furthermore, fails to deal with ventricular ectopic beats (VEB).

Accordingly, the main object of this invention is to reliably discriminate between normal sinus rhythm (NSR) and slow ventricular tachycardia (SLVT). The term SLVT encompasses both ventricular tachycardia with 1:1 retrograde conduction (VT1:1R) and slow dissociated ventricular tachycardia (SDVT).

It is another object of the invention to provide a classification technique which copes with ventricular ectopic beats (VEB).

Further objects and advantages of the invention will become apparent as the following description proceeds.

SUMMARY OF THE INVENTION

Briefly stated, and in accordance with one embodiment of the invention, there are provided an apparatus and method for discriminating between tachycardias of physiological origin, and those of pathological origin having similar atrial and ventricular rates. The apparatus includes two sensing electrodes for registering the electrograms from the atrium and the ventricle of the heart. There is further included a signal processing element for determining the times of atrial and ventricular events, and an algorithm for classifying the heart rhythm. The algorithm includes a means for discriminating between different types of heart rhythms having overlapping ventricular rates and having similar atrial and ventricular rates. The method utilizes an analysis of the relationships between successive atrial and ventricular intervals (i.e., atrial-atrial (AA), ventricular-ventricular (VV) and atrial-ventricular (AV) intervals) in discriminating between such heart rhythms.

BRIEF DESCRIPTION OF THE DRAWINGS

While the specification concludes with claims particularly pointing out and distinctly claiming the subject matter regarded as the invention herein, it is believed that the present invention will be more readily understood from the following description, taken in conjunction with the accompanying drawings, in which:

DETAILED DESCRIPTION OF THE INVENTION

Figure 1:
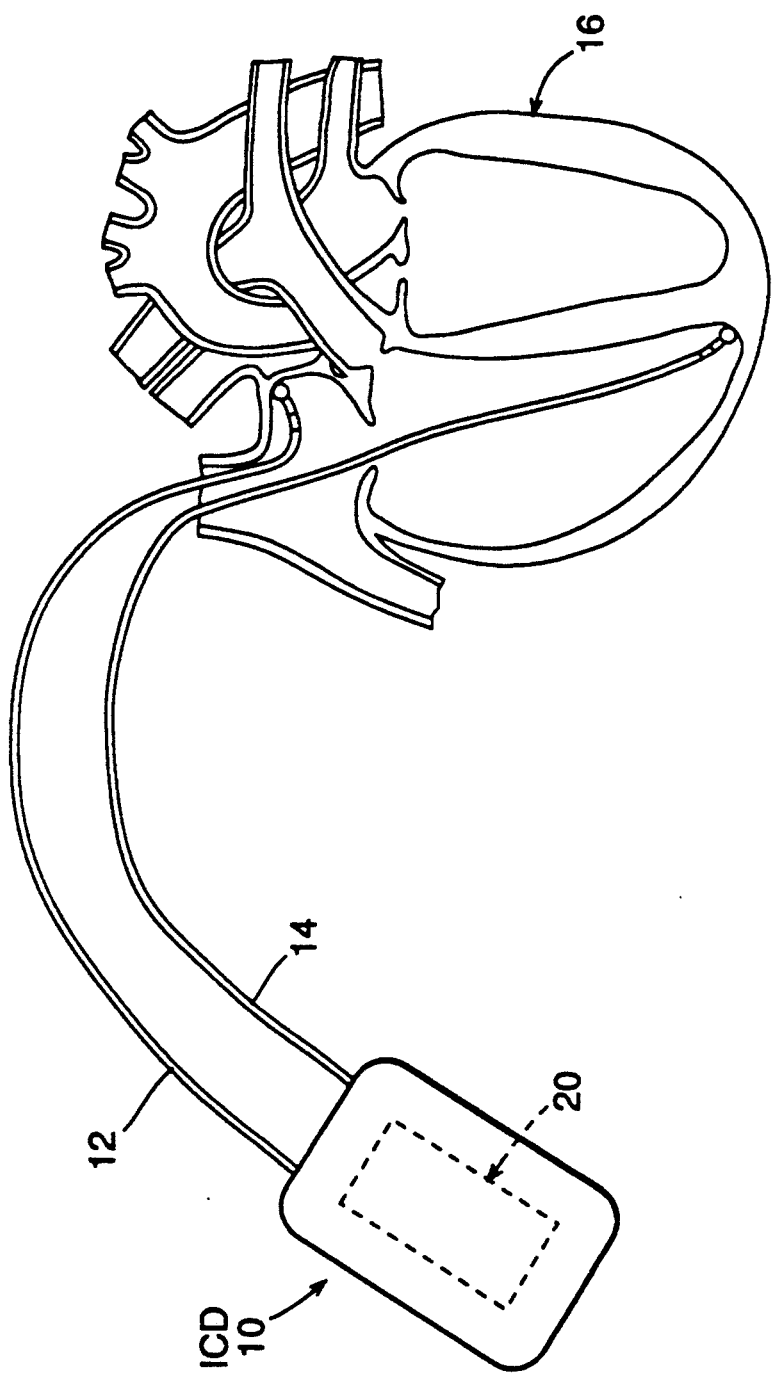
FIG. 1 depicts a block diagram of an implantable cardiac device employing atrial and ventricular sensing leads and including a functional module for heart rhythm classification.

Referring to FIG. 1, there is depicted a block diagram of an implantable cardiac device 10 having atrial and ventricular leads 12 and 14, respectively, connected to a patient's heart 16 for the sensing of atrial and ventricular events. Within the implantable cardiac device 10 is a functional module 20 for classification of sensed heart ventricular events.

Figure 2A:
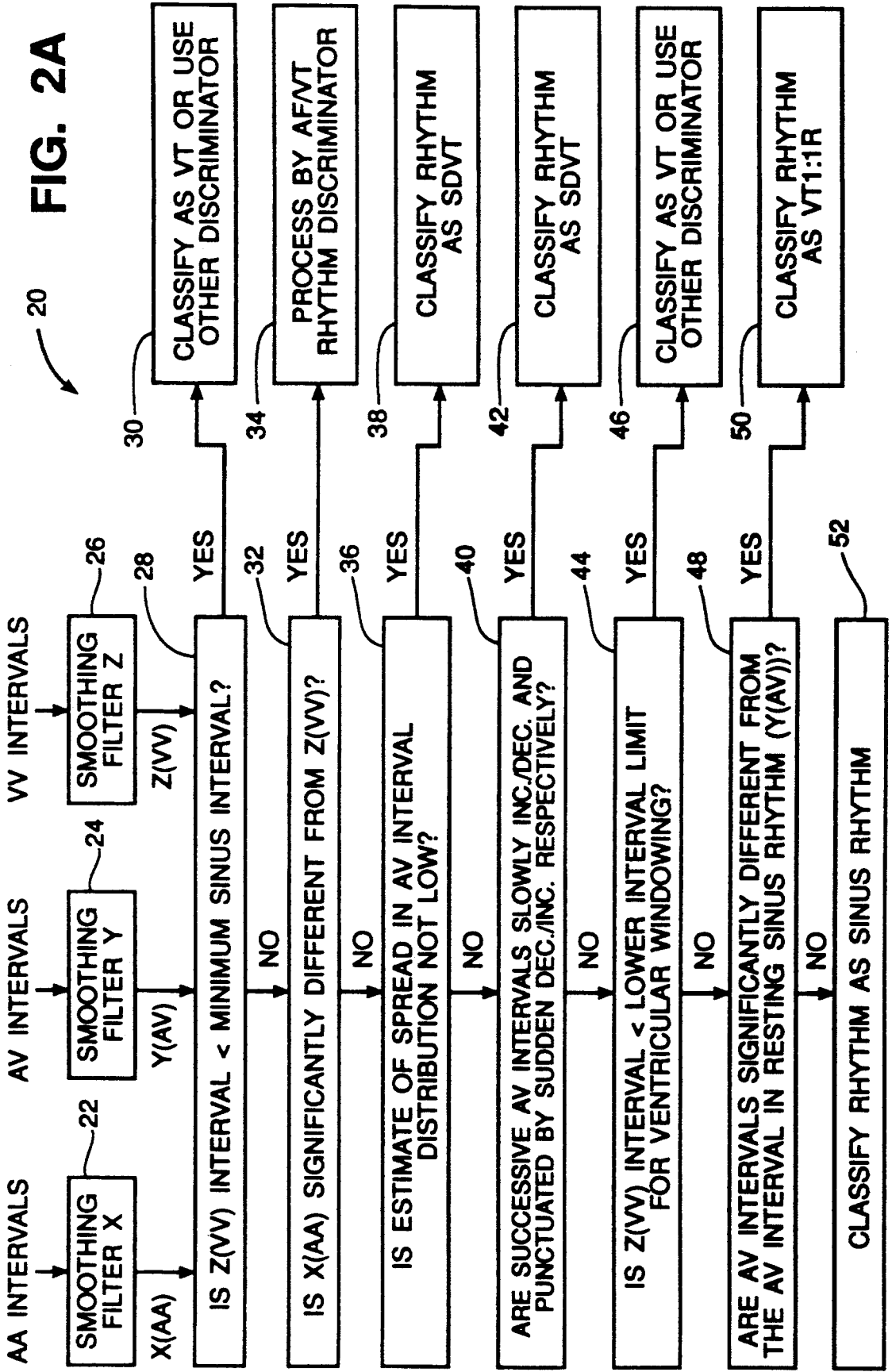
FIG. 2A and 2B show two alternative configurations of a technique in accordance with the present invention for discriminating between different rhythms having overlapping ventricular rates and having similar atrial and ventricular rates.
Figure 2B:
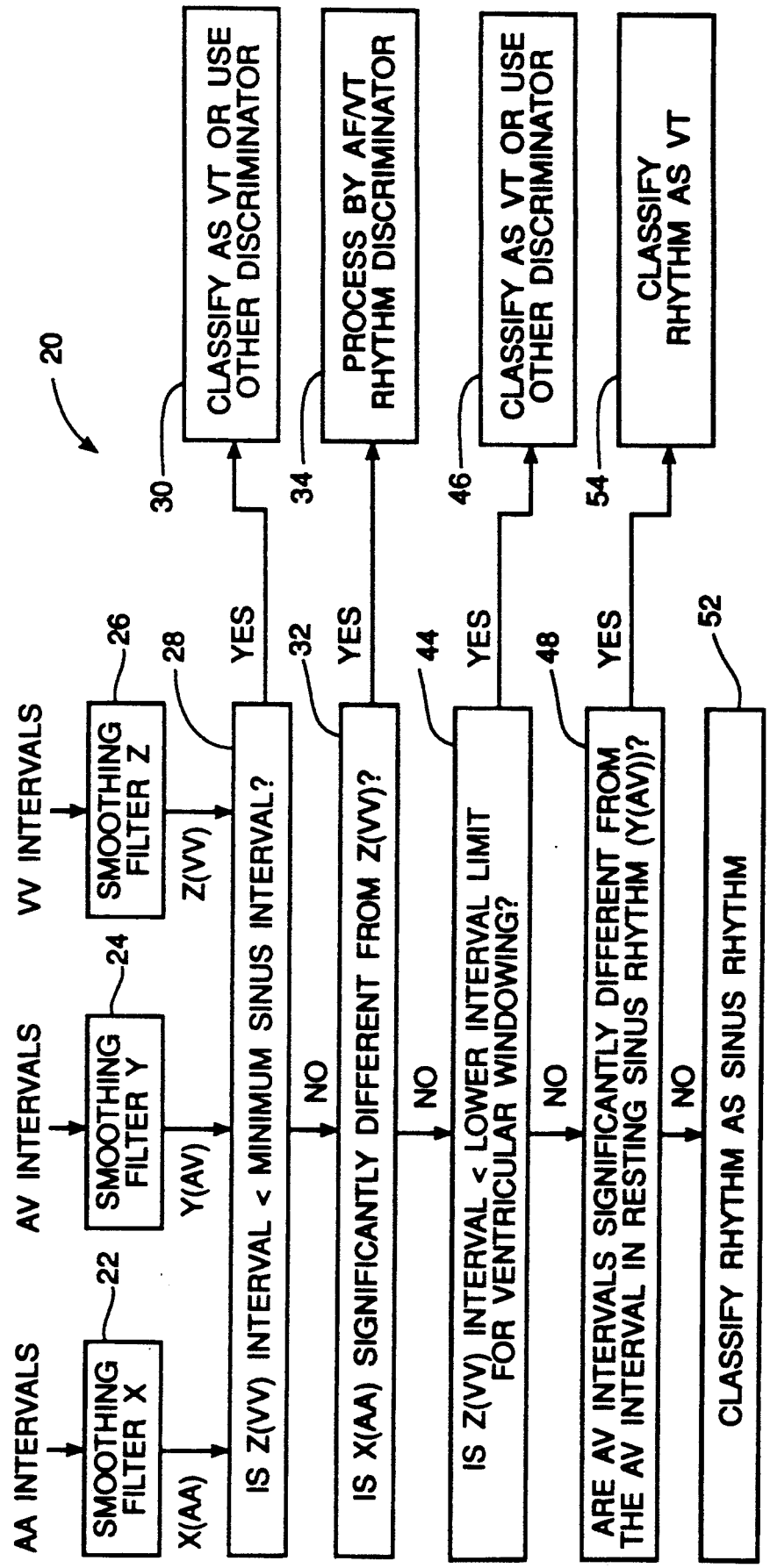

As indicated earlier, the different types of heart rhythms on which the invention is focused have similar atrial and ventricular rates, and overlapping ventricular rates. Referring now to FIGS. 2A and 2B, proposed schemes for discriminating between these different types of heart rhythms are disclosed. Alternative schemes may use only some of these elements, and the ordering of the elements employed in FIGS. 2A and 2B are not restricted to those shown in the examples.

The AA, AV and VV intervals determined by module 20 first need to be filtered in filters 22, 24 and 26 to suppress the effects of ectopic beats. A typical implementation of the X and Z filters 22 and 26, respectively, would take the last ten intervals as input and give their respective means as outputs. A typical implementation of the Y filter 24 would have as its output the sixth or seventh element in an ordered list of the last ten intervals (the input). This serves to solve the problem of discriminating AV intervals with ventricular beats of sinus origin (AVs) from those of ectopic origin (AVe) when the AVAV . . . sequence is preserved. This situation arises when ventricular ectopic beats occur so late after a sinus ventricular event that the atrioventricular conduction system of the ventricle is rendered refractory to the next sinus atrial event. The resulting AVsAVeAVsAVe . . . alternating sequence of sinus and ectopic ventricular beats is hereinafter referred to as "late" bigeminy. Noting that AVe<AVs, and that rarely more than half of AV intervals are AVe, the sixth or seventh element of an ordered list of AV intervals is almost certainly an AVs. This is useful in determining an AV interval reference for the ventricular windowing technique.

There is an upper rate (lower interval), represented by block 28, beyond which it is not physically feasible for the rhythm to be of sinus origin. Typically, this limit will be in the range of 170 to 200 bpm. Rhythms beyond this rate are classified as VT, as shown at block 30.

The remaining rhythms have their filtered AA and VV intervals ((X(AA) and Z(VV), respectively)) compared in order to separate out those heart rhythms with clearly dissimilar atrial and ventricular rates ((i.e., atrial fibrillation (AF) and ventricular tachycardia (VT)), as shown in block 32. AF and VT then need to be separated by a different rhythm discriminator, such as an A:V rate ratio, as shown in block 34.

In the configuration shown in FIG. 2A, the remaining rhythms with similar atrial and ventricular rates first have the spread of the distribution of a set of successive AV intervals assessed in order to separate out SDVT, as shown in block 36. This spread would typically be measured by the difference between two different elements in an ordered list of AV intervals; for example, the difference between the ninth and second elements in an ordered list of the last ten AV intervals. If this spread is not low, then this heart rhythm is classified as SDVT, as shown in block 38.

Figure 3A:
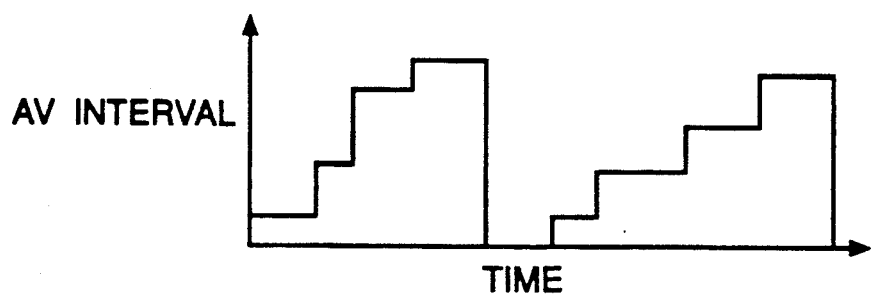
FIGS. 3A-3C show the respective general patterns in atrial-ventricular (AV) interval waveforms for SDVT when the atrial rate is less than the ventricular rate, the atrial rate is greater than the ventricular rate, and for normal sinus rhythm.
Figure 3B:
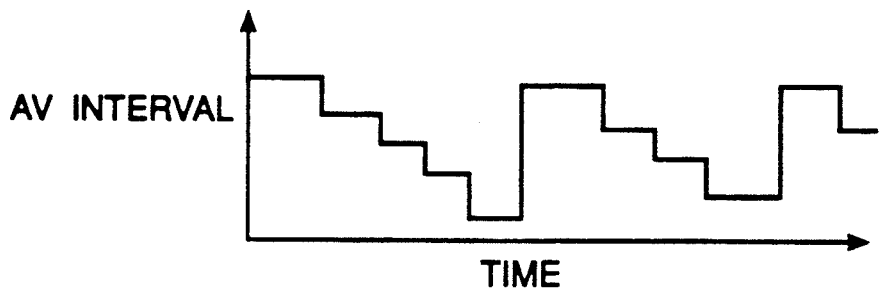
Figure 3C:
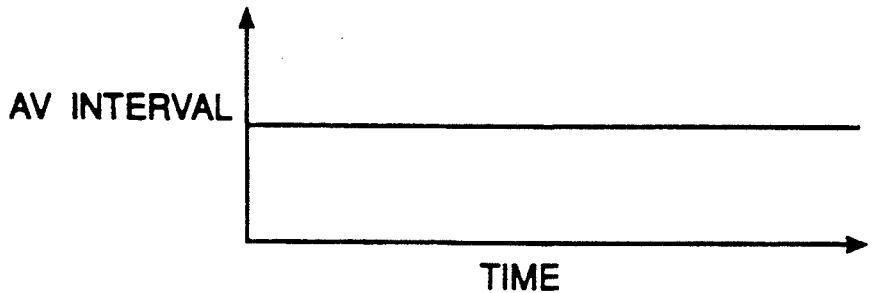

The next step in FIG. 2A separates out SDVT with small differences between the atrial and ventricular rates by measuring changes in successive AV intervals, as shown in block 40. If these changes follow a periodic pattern of slow increases/decreases punctuated by fast decreases/increases, respectively, as depicted in FIGS. 3A and 3B, then the rhythm is identified as SDVT, as shown in block 42.

Figure 5:
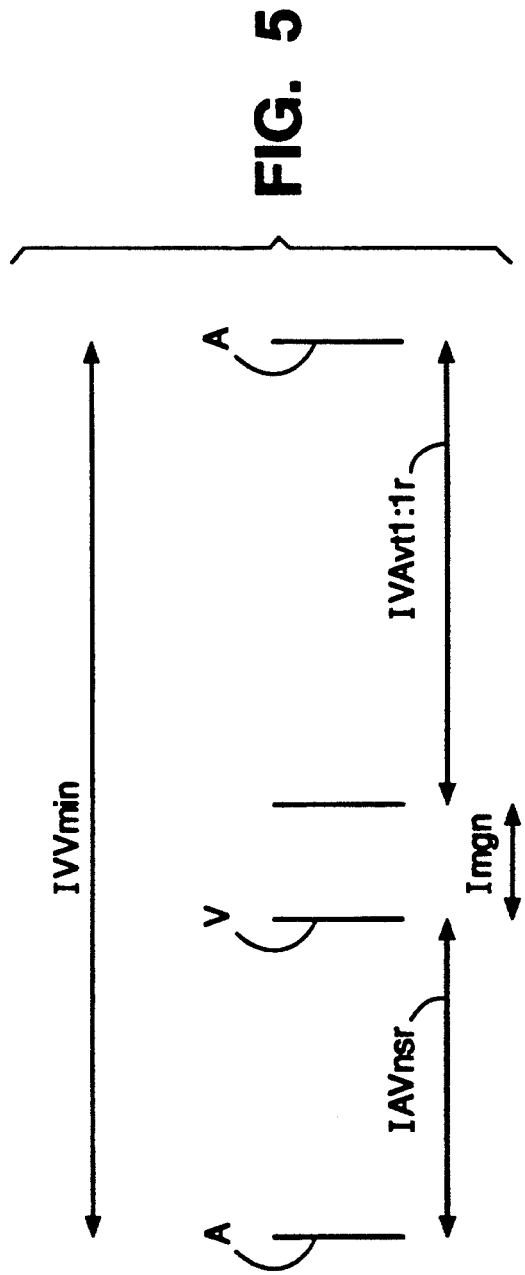

The remaining different rhythm classifications in FIG. 2A are normal sinus rhythm (NSR) and ventricular tachycardia with 1:1 retrograde conduction (VT1:1R). In FIG. 2B the remaining different rhythm classifications at a corresponding point (input to block 44) are normal sinus rhythm (NSR) and ventricular tachycardia (either VT1:1R or SDVT). The proposed technique for discrimination between these rhythms will work reliably if the ventricular interval exceeds a lower limit, as shown in block 44. Referring to FIG. 5, this limit is defined by the ventricular interval rate IVVmin, which is given by the sum of the AV interval in normal sinus rhythm, IAVnsr, and the VA interval in VT1:1R, IVAvt1:1r plus an interval margin Imgn (typically 45 msec), as depicted in FIG. 5. If the output Z(VV) of filter 26 (FIG. 2) is less than this lower limit, the rhythm is classified as VT, or is processed by a different rhythm discriminator, as shown in block 46. It is only when this lower limit on the Z(VV) interval value is greater than the minimum sinus interval that it is possible for the rhythm discriminator of block 46 to be invoked.

Figure 4:
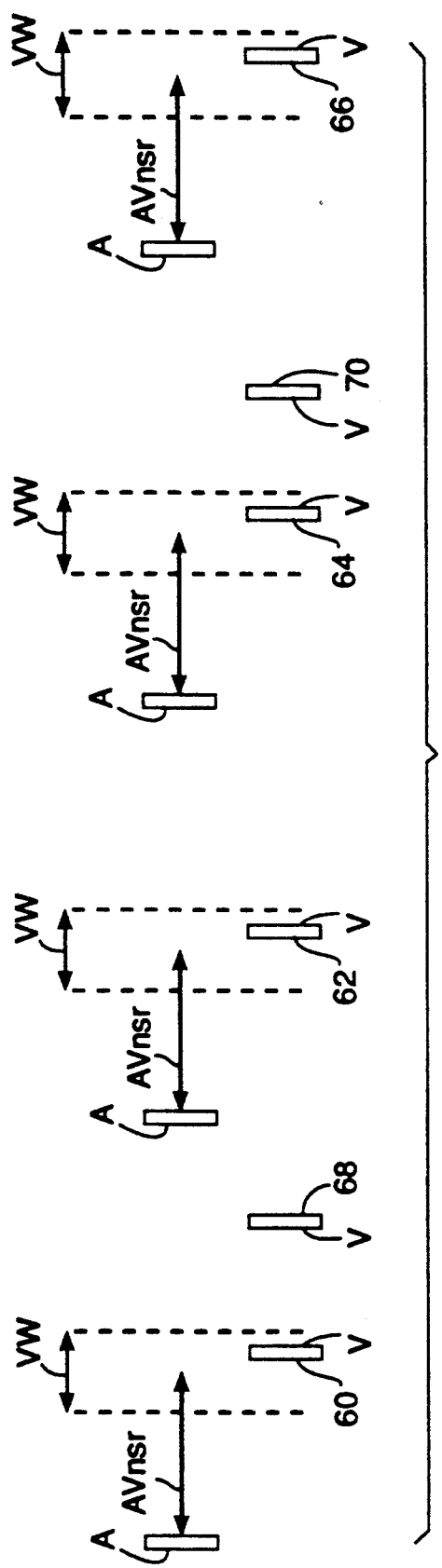
FIG. 4 depicts the atrial and ventricular sense events and the parameters involved in determining significant similarity of a given rhythm to normal sinus rhythm; and, FIG. 5 defines a minimum ventricular interval for reliable performance of a ventricular windowing technique employed in this invention.

Referring to FIG. 4 there are depicted the atrial and ventricular sense events and the parameters involved in determining significant similarity of a given rhythm to a normal sinus rhythm. Note that except where stated otherwise, an AV interval is defined to be the interval between an atrial event A, and an immediately following ventricular event V with no intervening atrial event. This definition of AV interval filters out ventricular ectopic beats which occur after a sinus ventricular event but before the next sinus atrial event, hereafter referred to as "early" ventricular ectopic beats (VEB). Bigeminy in which the VEBs are early are hereafter referred to as "early bigeminy". Alternative realizations may employ a definition of AV interval that includes the intervals between an atrial event and two or more following ventricular events, with no intervening atrial events. A ventricular window VW is placed about the AV intervals observed in normal sinus rhythm. The AV intervals observed in normal sinus rhythm AVnsr are such that the window VW encompasses the range of AV intervals seen in sinus tachycardia, as shown at 60, 62, 64 and 66. This will typically be from $-50$ to $+45$ msec about AVnsr. AV intervals within the ventricular window VW range are characteristic of sinus rhythm. AV intervals outside the VW range are classified as non-sinus. If a large enough proportion of AV intervals are non-sinus, the diagnosis of VT1:1R or SDVT is made, provided other conditions are met.

The AV interval reference AVnsr may be derived from Y(AV) by calculating the sixth or seventh element in a set of ten successive AV intervals, as explained in connection with FIGS. 2A and 2B, above. As indicated earlier, the AV interval is defined to be the interval between an atrial event A and the first immediately following ventricular event V. Accordingly, any second or later following ventricular events, such as those shown at 68 and 70, are ignored in the determination of the AV interval reference AVnsr.

This technique, referred to as "ventricular windowing", effectively characterizes sinus rhythm. Referring back to FIG. 2A, if the filtered AV intervals from filter 24 predominantly fall outside the defined ventricular window, as shown in block 48, then the rhythm is identified as VT1:1R, as shown in block 50; otherwise, it is classified as sinus rhythm, as shown in block 52 (FIG. 2A). Alternatively, referring to FIG. 2B, if another discriminator is not used to identify SDVT in block 46, and intervals are predominantly outside VW, the diagnosis of VT (e.g., either SDVT or VT1:1R) is made in block 54. Typically, at least seven of the last ten AV intervals must be outside the ventricular window for the rhythm to be classified either as VT1:1R in block 50 of FIG. 2A or as VT in block 52 of FIG. 2B. This mode of operation is necessary because "late" bigeminy needs to be classified as sinus rhythm (SR). In "late" bigeminy, as described above for the Y filter of FIG. 2A, 5 of the last 10 AV intervals are outside of the ventricular window. The AV intervals associated with the ventricular ectopic beats in "late" bigeminy are shorter than the sinus beats; hence the upper 50% of the AV intervals will be sinus AV intervals. The sixth/seventh elements are used to give some safety margin.

It will be apparent from the foregoing discussion that the present invention provides an apparatus and method that reliably discriminate between normal sinus rhythm and slow ventricular tachycardia, including ventricular tachycardia with 1:1 retrograde conduction and slow dissociated ventricular tachycardia. Moreover, the classification technique successfully copes with ventricular ectopic beats in performing its function.

While particular embodiments of this invention have been shown and described, it will be obvious to those skilled in the art that various other changes and modifications may be made without departing from the invention in its broader aspects, and it is, therefore, aimed in the appended claims to cover all such changes and modifications as fall within the true spirit and scope of this invention.

What is claimed is:

1. An implantable medical device for monitoring and classifying cardiac rhythms of a patient's heart, comprising:
    means for sensing atrial and ventricular events of the heart;
    means for measuring intervals "AV" between atrial and ventricular contractions of the heart;
    means for measuring and storing "AVnsr", the AV internal of the patient's heart rhythm during resting normal sinus rhythm thereof;
    means for classifying said rhythms based on the timing of said sensed events;
    said classifying means including means for discriminating between tachycardias of physiological origin and tachycardias of pathological origin having overlapping ventricular rates, each of said tachycardia's having similar atrial and ventricular rates and each of said tachycardias having ventricular-ventricular intervals which are less than a predetermined minimum normal sinus interval, said discriminating means including means for forming an interval timing window having a first predetermined threshold shorter than said AVnse interval and a second predetermined threshold longer than said AVnsr interval;
    said classifying means including mean for classifying as pathological origin those of said tachycardias in which the Av intervals fall outside of said interval timing window; and
    said device further including means for utilizing the results of said classifying means.

2. A device according to claim 1, wherein said means for classifying tachycardias as of pathological origin requires that a predetermined number of most recent AV intervals fall outside of said interval timing window in order to classify a tachycardia as pathological.

3. A device according to claim 2, wherein said means for classifying tachycardias as of pathological origin also requires that a predetermined proportion of said most recent AV intervals fall outside of said interval timing window in order to classify a tachycardia as pathological.

4. A device according to claim 1, wherein said means for classifying tachycardias as of pathological origin requires that a predetermined proportion of most recent AV intervals fall outside of said interval timing window in order to classify a tachycardia as pathological.

5. A device according to claim 1, further including means for precluding said classifying means from classifying said tachycardias on the basis of AV intervals if the ventricular-ventricular intervals are below a predetermined threshold.

6. A device according to claim 1, further including means for precluding said classifying means from classifying said tachycardias on the basis of AV intervals if the atrial-atrial intervals exceed the ventricular-ventricular intervals by more than a predetermined amount.

7. A device according to any one of claims 1, and 2–6, further including means for calculating said AVE interval during resting normal sinus rhythm as a predetermined order entry in an ordered list of a predetermined number of successive AV intervals measured during resting normal sinus rhythm.

8. A device according to claim 7, wherein said predetermined order entry is an entry selected from the sixth and seventh entries, and the predetermined number of successive AV intervals measured during resting normal sinus rhythm is ten, so that the calculated AV interval is resting normal sinus rhythm is derived as the sixth or seventh entry in said ordered list of ten successive AV intervals measured during resting normal sinus rhythm.

9. A device according to claim 6, further including means for precluding said classifying means from classifying said tachycardias on the basis of AV intervals if the ventricular-ventricular intervals exceed the atrial-atrial intervals by more than a predetermined amount.

10. A method of monitoring and classifying cardiac rhythms of a patient's heart comprising the steps of:
    sensing atrial and ventricular events of the heart;
    measuring intervals "AV" between atrial and ventricular contractions of the heart;
    measuring and storing "AVnse", the AV interval of the patient's heat rhythm during resting normal sinus rhythm thereof;
    forming an interval timing window having a first predetermined threshold shorter than said AVnsr interval and a second predetermined threshold longer than said AVnsr interval;
    discriminating between tachycardias of physiological origin and tachycardias of pathological origin having overlapping rates, each of said tachycardias having similar atrial and ventricular rates and each of said tachycardias having ventricular-ventricular intervals which are less than a predetermined minimum normal sinus interval, by classifying as of pathological origin those of said tachycardias in which the AV intervals of the cardiac rhythm fall outside of said interval timing window; and
    utilizing the results of said discriminating step.

11. A method according to claim 10, wherein said discriminating step includes a sub-step of determining that a predetermined number of most recent AV intervals fall outside of said interval timing window before classifying a tachycardia as pathological.

12. A method according to claim 11, wherein said discriminating step includes a further sub-step of determining that a predetermined proportion of said most recent AV intervals fall outside of said interval timing window before classifying a tachycardia as pathological.

13. A method according to claim 10, wherein said discriminating step includes a sub-step of determining that a predetermined proportion of most recent AV intervals fall outside of said interval timing window before classifying a tachycardia as pathological.

14. A method according to claim 10, including the further step of precluding said discriminating step from classifying said tachycardias on the basis of AV intervals if the ventricular-ventricular intervals are below a predetermined threshold.

15. A method according to claim 10, including the further step of precluding said discriminating step from classifying said tachycardias on the basis of AV intervals if the atrial-atrial intervals exceed the ventricular-ventricular intervals by more than a predetermined amount.

16. A method according to any one of claim 10, and 11-15, including a step of calculating said AV interval during resting normal sinus rhythm as a predetermined order entry in an ordered list of a predetermined number of successive A-V intervals measured during resign normal sinus rhythm.

17. A method according to claim 16, including substeps of selecting said predetermined order entry from one of said sixth and seventh entries, and utilizing ten successive AV intervals measured during resting normal sinus rhythm as said predetermined number of successive AV intervals, so that the calculated AV interval in resting normal sinus rhythm is derived as a sixth or seventh entry in said ordered list of ten successive AV intervals measured during resting normal sinus rhythm.

18. A method according to claim 15, including the further step of precluding said discriminating step from classifying said tachycardias on the basis of AV intervals if the ventricular-ventricular intervals exceed the atrial-atrial intervals by more than a predetermined amount.

* * * * *